United States Patent [19]

Inoue et al.

[11] 3,944,605

[45] Mar. 16, 1976

[54] METHOD OF RECOVERING UNREACTED AMMONIUM CARBAMATE IN UREA SYNTHESIS

[75] Inventors: Shigeru Inoue; Tetsuo Kimura, both of Kamakura, Japan

[73] Assignee: Mitsui Toatsu Chemicals, Inc., Tokyo, Japan

[22] Filed: Jan. 28, 1974

[21] Appl. No.: 437,360

[30] Foreign Application Priority Data

Feb. 14, 1973 Japan................................ 48-17518

[52] U.S. Cl............................................. 260/555 A
[51] Int. Cl.$^2$................................... C07C 126/00
[58] Field of Search................................ 260/555 A

[56] References Cited
UNITED STATES PATENTS

| | | | |
|---|---|---|---|
| 3,544,628 | 12/1970 | Hsu...................................... | 260/555 |
| 3,573,173 | 3/1971 | Otsuka et al........................ | 260/555 |

*Primary Examiner*—James O. Thomas, Jr.
*Assistant Examiner*—A. Siegel

[57] ABSTRACT

Unreacted ammonium carbamate contained in urea synthesis effluent obtained by reacting ammonia and carbon dioxide at urea synthesis pressures and temperatures is recovered by a method comprising subjecting the urea synthesis effluent to a three-stage decomposition to decompose the unreacted ammonium carbamate in each stage, the first stage and the second stage of which are operated at a gauge pressure of at least 30 kg/cm$^2$ and a gauge pressure of from 10 to 25 kg/cm$^2$, respectively, absorbing the off-gas resulting from the second stage decomposition in an absorbent to form an aqueous solution of ammonium carbamate and unabsorbed gaseous ammonia, condensing the gaseous ammonia to form recovered liquid ammonia, and absorbing substantially all of the off-gas resulting from the first stage decomposition in the aqueous solution of ammonium carbamate to form recovered ammonium carbamate solution while removing the heat of absorption by indirect heat exchange with the recovered liquid ammonia pressurized to the urea synthesis pressure.

5 Claims, 1 Drawing Figure

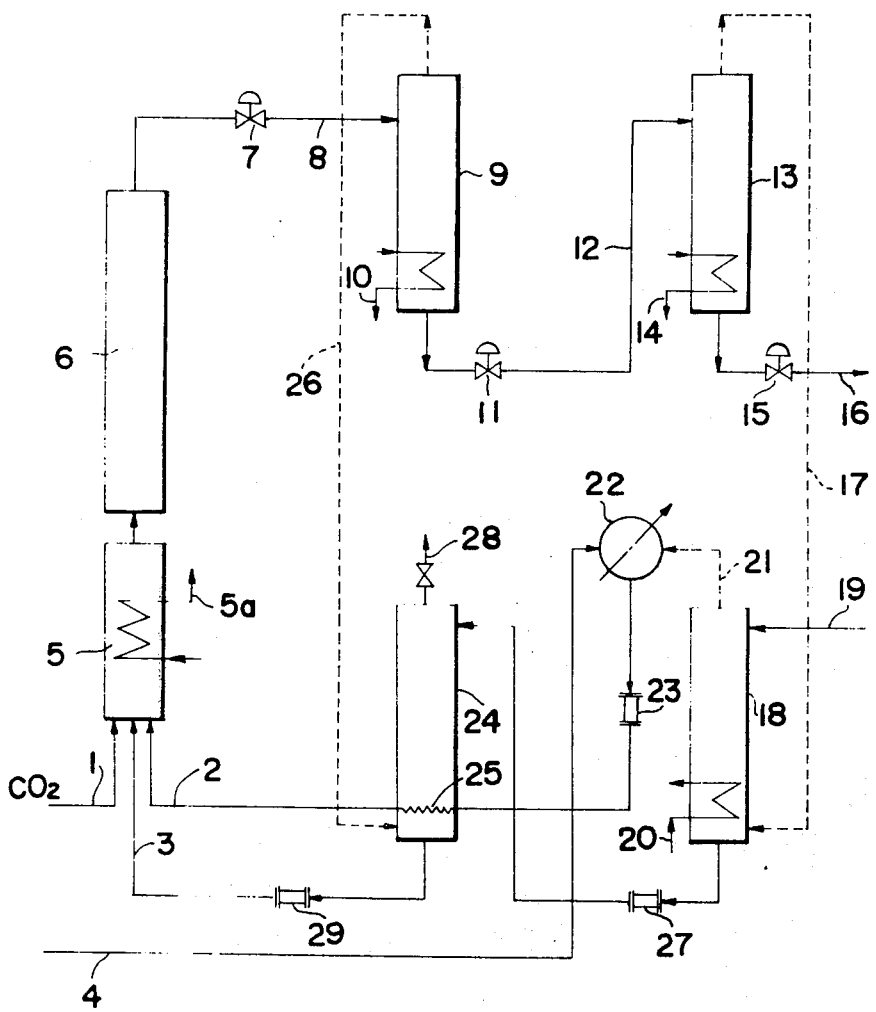

METHOD OF RECOVERING UNREACTED AMMONIUM CARBAMATE IN UREA SYNTHESIS

BACKGROUND OF THE INVENTION

1. Field of the Invention

This invention relates to an improved method for the recovery of unreacted ammonium carbamate in the production of urea from carbon dioxide and ammonia.

2. Description of the Invention

Several methods for the preparation of urea from ammonia and carbon dioxide are known in the art, including a solution recycle process wherein unreacted ammonium carbamate is recovered in the form of an aqueous solution for recirculating to a urea synthesis stage. Particularly, there has been widely employed a total recycle process with solution recycle wherein the effluent from the urea synthesis stage is passed through high pressure and low pressure decomposition stages for decomposing unreacted ammonium carbamate. The off-gas resulting either from the high pressure decomposition stage or from both the high and low pressure decomposition stages is absorbed in an absorbent, while discharging unabsorbed excess ammonia from the high pressure absorption stage to be liquefied by water cooling. The recovered ammonium carbamate solution and the liquid ammonia are, respectively, recirculated to the urea synthesis stage. The two-stage decomposition and two-stage absorption system has, however, a disadvantage, in that the excess heat generated in the high pressure absorption stage cannot be recovered in an efficient manner. That is, the absorption of off-gas is effected under high pressure decomposition conditions using a gauge pressure of from 15 to 20 kg/cm$^2$ at an absorption temperature of about 100°C. Accordingly, the recovered ammonium carbamate solution which is recirculated to the urea synthesis stage is at a temperature which is low as compared with a conventional urea synthesis temperature of from 160° to 200°C. Additionally, temperatures of make-up liquid ammonia and of recovered liquid ammonia are as low as below 50°C, so that the excess heat to be recovered in the urea synthesis stage is reduced.

In order to overcome the disadvantage, U.S. Pat. No. 3,573,173 proposes a method of effecting the decomposition of unreacted ammonium carbamate and absorption of the resulting off-gas in three stages, i.e., a first stage having a gauge pressure greater than 30 kg/cm$^2$, preferably greater than 60 kg/cm$^2$, and second and third stages with pressures as in the conventional two-stage high and low pressure decomposition and absorption, with the result that a recovered ammonium carbamate solution has a temperature of 120°–180°C. According to this method, however, the decomposition and absorption are effected in three stages and excess ammonia which is not absorbed in each of the absorption stages of the off-gases from the first decomposition stage and second decomposition stage is discharged in the form of a gas. Thus, it is undesirably required to liquefy the ammonia gases by means of additional condensers. In this connection, the process of U.S. Pat. No. 3,573,173 is considered however somewhat advantageous in that ammonia gas contained in the off-gas from the first decomposition stage and not absorbed in the absorption of the off-gas can be recovered in the form of a relatively high temperature liquid ammonia by mixing it with make-up liquid ammonia.

It is generally technically difficult to make the amount of carbon dioxide contained in the excess ammonia unabsorbed in a high pressure absorption stage, substantially equal to zero. The difficulty increases with an increase in the absorption pressure since the increase of absorption pressure results in an elevation of the absorption temperature and accordingly the partial pressure of carbon dioxide in the resultant absorbate is raised. In order to overcome this difficulty, it is undesirably required to use an absorption column of complicated construction. Alternatively, the leakage of carbon dioxide can be prevented by lowering the temperature at the top of the absorption column by feeding liquid ammonia to the top of the column to remove the heat of absorption by evaporation of the liquid ammonia. However, the evaporated ammonia has to be then liquefied in a condenser for recirculation to the top of the column, this inviting difficulties in the operation and in the structural designing of the column.

As it will be apparent from the foregoing, when the absorption pressure is increased, it becomes more difficult to make the amount of carbon dioxide contained in the excess ammonia generated in the absorption stages substantially equal to zero. Moreover, the greater the pressure of the decomposition stage, the less is the amount of the off-gas, which is separated from the urea synthesis effluent in the decomposition stage. In this instance, when urea synthesis effluent which is obtained by reacting carbon dioxide with ammonia in a stoichio-metric excess of 100 percent (molar ratio of NH$_3$ to CO$_2$ of 4), is subjected to decomposition of unreacted ammonium carbamate at a gauge pressure of 17 kg/cm$^2$, and the resultant off-gas is absorbed in an absorbent, the amount of ammonia which is not absorbed in the absorption stage rises to more than 60 percent by weight of the total ammonia contained in the urea synthesis effluent. On the other hand, when a urea synthesis effluent having the same composition as mentioned above is subjected to unreacted ammonium carbamate decomposition at a gauge pressure of 65 kg/cm$^2$ and the resultant off-gas is absorbed, the amount of ammonia which is not absorbed in the absorption stage is as low as about 10 percent by weight of the total amount of ammonia contained in the urea synthesis effluent. In other words, the amount of ammonia absorbed is about 4 times that of unabsorbed ammonia.

SUMMARY OF THE INVENTION

It is an object of the present invention to provide an improved process for recovering unreacted ammonium carbamate.

It is another object of the present invention to provide a process for recovering unreacted ammonium carbamate while preheating recovered and/or make-up liquid ammonia.

It is still another object of the present invention to provide a process for recovering unreacted ammonium carbamate while obtaining a high-temperature recovered ammonium carbamate solution.

It is a further object of the present invention to provide a process for the preparation of urea with favorable heat recovery in the urea synthesis stage.

Briefly stated, in the present invention, urea is prepared in the presence of an excess ammonia. That is, a molar ratio of total NH$_3$ to total CO$_2$ used in the synthesis stage is preferably in the range of from 2.5 to 6. Urea synthesis is preferably conducted at a pressure of from 150 to 300 kg/cm² and a temperature of from 160° to 210°C.

The effluent discharged from a urea synthesis reactor is subjected to a three-stage decomposition of unreacted ammonium carbamate. The first stage (which will be hereinafter referred to as a high pressure separation stage) is maintained at a gauge pressure of above 30 kg/cm², preeferably, from 40 to 120 kg/cm², at a temperature of, preferably, above 130°C, particularly, from 140° to 180°C. In the first stage, a portion of the excess ammonia and a portion of the unreacted ammonium carbamate are separated from the reaction solution in the form of a gaseous mixture (off-gas) of ammonia, carbon dioxide and water vapor.

The depleted urea synthesis effluent thus treated is then introduced into the second stage (which will be hereinafter referred to as a medium pressure distillation stage) for further decomposition of the remaining unreacted ammonium carbamate. The second stage is maintained at a gauge pressure of from 10 to 25 kg/cm² and a temperature of, preferably, from 140° to 170°C. In the second stage, almost all of the excess ammonia and a major part of the remaining ammonium carbamate are separated in the form of a gaseous mixture (off-gas) of ammonia, carbon dioxide and water vapor.

However, the urea solution from the second stage still contains unreacted ammonium carbamate and ammonia in a total amount of less than 10 percent by weight, and is therefore introduced into a third stage (which will be hereinafter referred to as a low pressure distillation stage) to completely decompose the remaining ammonium carbamate. The third stage has a gauge pressure of less than 5 kg/cm² and a temperature of, preferably, from 110° to 140°C. In the third stage, all of the remaining ammonium carbamate and ammonia are separated in the form of a gaseous mixture (off-gas) containing ammonia, carbon dioxide and water vapor.

The off-gas generated in the second stage is introduced into a medium pressure absorption stage where the off-gas is absorbed in an absorbent such as water or an aqueous solution. The off-gas from the third stage may be absorbed in an absorbent prior to the introduction into the medium pressure absorption stage. In the medium pressure absorption stage substantially all of the carbon dioxide contained in the off-gas from the second stage and a portion of the ammonia are absorbed, and the remaining unabsorbed ammonia is discharged in the form of a gas from the top of the absorption column. The ammonia gas is liquefied by water cooling to form recovered liquid ammonia. Alternatively, the ammonia gas may be mixed with make-up liquid ammonia liquid ammonia as a starting material and then cooled with water. In this connection, when make-up liquid ammonia has a low temperature, the cooling water can be saved for liquefying the ammonia gas from the medium pressure absorption stage.

The absorbate discharged from the medium pressure absorption stage is then fed to the high pressure absorption stage to absorb therein substantially all of the off-gas from the first stage to obtain the recovered ammonium carbamate solution. The temperature of the high pressure absorption stage is maintained, preferably, at 130° to 160°C by passing the recovered liquid ammonia pressurized to the urea synthesis pressure through a cooler (or a heat exchanger) provided in the high pressure absorption column. The recovered liquid ammonia may be mixed with the make-up liquid ammonia prior to being passed through the cooler. The recovered liquid ammonia is heated by the heat of absorption to a temperature of, preferably, from 100° to 160°C, particularly 110° to 140°C. The heated liquid ammonia and the recovered ammonium carbamate solution are recirculated to the urea synthesis reactor.

In the present invention, the urea synthesis stage is preferably composed of a heat recovery stage and a synthesis stage. In the heat recovery stage, there is provided a heat exchanger for removing the heat of reaction of ammonia with carbon dioxide. The heat of reaction is utilized for generation of steam or for decomposition of unreacted ammonium carbamate by passing the urea synthesis effluent through the heat exchanger under reduced pressure.

The heat of absorption generated in the medium pressure absorption column is generally removed by water cooling, heat-exchange with an aqueous urea solution to be concentrated, or by the combination of these means. Concurrently, the ammonia gas is discharged from the medium pressure absorption column and, if desired, mixed with make-up liquid ammonia and liquefied by water cooling. The resultant liquid ammonia may be preheated by heat exchange with the heat of absorption generated in the medium pressure absorption column, prior to introduction into the cooler (heat exchanger) of the high pressure absorption column.

Thus, a first advantage of the present invention is that the temperature of the recovered ammonium carbamate solution which is circulated to the urea synthesis stage can be raised to a sufficiently high degree, so that the heat balance of the urea synthesis stage is maintained in a satisfactory condition for recovering surplus heat.

A second advantage of the present invention resides in that, prior to being introduced into the urea synthesis stage, the recovered liquid ammonia (and make-up liquid ammonia) can be preheated by means of the heat of absorption which is generated in the high pressure absorption stage; the preheated liquid ammonia advantageously contributing to maintain the heat balance of the synthesis stage in a favorable condition for the recovery of surplus heat generated in the urea synthesis stage.

A third advantage of the present invention is that the process can be effected by the use of a relatively simple system which comprises a high pressure separator and a high pressure absorption column in combination with a conventional two-stage decomposition and two-stage absorption, thus being advantageous from structural, design and operational points of view. That is, no other expensive additional apparatus such as a condenser is required in the high pressure absorption stage since substantially all of the ammonia gas is absorbed in this stage. Furthermore, there is not required a column having such complicated structure as is usually required in the liquefaction and recovery of unabsorbed ammonia for suppressing the leakage of carbon dioxide which would otherwise be discharged along with ammonia gas. Additionally, the number of booster pumps and the boosting ratio for make-up and recovered liquid ammonia are the same as in the conventional two-stage systems. The compression of liquid ammonia can be effected at room temperature, so that a centrifugal pump can be employed for the compression.

Thus, the disadvantages which would otherwise result from the need for an additional apparatus and slightly complicated operations are sufficiently compensated by the improvement in the heat balance in the synthesis stage, i.e., the surplus heat generated in the absorption stages can be efficiently recovered in the synthesis stage.

BRIEF DESCRIPTION OF THE DRAWING

The sole FIGURE is a flow-sheet diagram illustrating a method for embodying the present invention.

DESCRIPTION OF SPECIFIC EMBODIMENTS

The present invention will be particularly described in connection with the accompanying illustrative and non-limiting drawing. In the drawing, carbon dioxide, line 1, which is held at the urea synthesis pressure (preferably, a gauge pressure of from 150 to 300kg/cm$^2$), liquid ammonia, line 2, which is held at the urea synthesis pressure and which is preheated as described hereinafter, and recovered ammonium carbamate solution, line 3, which is also maintained at the urea synthesis pressure, are fed into heat recovery zone 5, respectively. The heat recovery zone 5 is provided with cooler 5a for recovering surplus heat of reaction to generate steam having a gauge pressure of from 2 to 6 kg/cm$^2$. The quantity of heat removable in the heat recovery zone 5 depends upon the temperature of the synthesis zone 6. The reaction mixture discharged from the heat recovery zone 5 is then introduced into the urea synthesis zone 6 for converting ammonium carbamate into urea. The urea synthesis zone 6 is preferably maintained at a temperature of from 160° to 210°C, and the molar ratio of total ammonia to total carbon dioxide to be introduced into the synthesis zone 6 is preferably in a range of from 2.5 to 6.

The resultant urea synthesis effluent which is composed of urea, water, excess ammonia and unreacted ammonium carbamate is depressurized to a gauge pressure greater than 30 kg/cm$^2$, preferably, of from 40 to 120 kg/cm$^2$, through let-down valve 7 and introduced into high pressure separator 9 through line 8. In the separator 9, a portion of the excess ammonia and of the unreacted ammonium carbamate is separated from the urea synthesis effluent in the form of a gaseous mixture (off-gas) containing ammonia, carbon dioxide and water vapor. The urea synthesis effluent in the high pressure separator is maintained at a temperature higher than 130°C, preferably, of from 140° to 180°C, by heating by means of heater 10, if necessary.

The depleted urea synthesis effluent from the high pressure separator 9 is reduced in pressure by means of reducing valve 11 to a gauge pressure of from 10 to 25 kg/cm$^2$, and is introduced into medium pressure distillation column 13 through line 12. In the column 13, the depleted urea synthesis effluent is heated to a temperature of from 140° to 170°C by means of heater 14 for separating the major part of the unreacted ammonium carbamate from the depleted urea synthesis effluent as an off-gas comprising ammonia, carbon dioxide and water vapor. The urea solution from the column 13 still contains unreacted ammonium carbamate in an amount less than 10 percent by weight, and is further reduced in pressure by means of reducing valve 15 to a gauge pressure of from 0 to 5 kg/cm$^2$. The urea solution having the pressure reduced is passed through line 16 and is subjected to a conventional low pressure distillation (not shown) for separating the remaining ammonium carbamate from the urea solution to obtain a urea solution substantially free from ammonium carbamate.

The thus obtained urea solution is treated by any known finishing process to obtain a urea product in the form of a crystal or prill.

Concurrently, the off-gas which is generated from the medium pressure distillation column 13 is fed to medium pressure absorption column 18 through line 17. In the absorption column 18 there is introduced an absorbent (which may be an absorbate obtained by absorbing the off-gas from the low pressure distillation in water, an aqueous ammonia solution or an aqueous urea solution) through line 19 to absorb the off-gas. The absorption pressure is substantially the same as that of the medium pressure distillation column and the absorption temperature at the bottom of the column 18 is maintained at a temperature of from 90° to 110°C with the aid of cooler 20. Gaseous excess ammonia which is not absorbed in the absorbent is then fed through line 21 into ammonia condenser 22, in which the gaseous ammonia is mixed with make-up liquid ammonia which is introduced through the line 4 into the ammonia condenser 22. The mixture is cooled with water to a temperature of from 20° to 50°C for condensation.

A portion of the liquid ammonia which is formed in the ammonia condenser 22 may be circulated to the top of the medium pressure absorption column 18 to decrease the temperature at the top of the column. The remaining liquid ammonia is compressed to the urea synthesis pressure by means of pump 23 and thereafter is passed through cooler 25 of the high pressure absorption column 24. The liquid ammonia is preheated as will be described hereinafter and is then introduced into the heat recovery zone 5 through the line 2 as described hereinbefore.

The off-gas from the high pressure separator 9 is fed to the high pressure absorption column 24 through line 26. Into the high pressure absorption column 24 is introduced the absorbate which is discharged from the medium pressure absorption column 18 and pressurized to the pressure of the column 24 (i.e., a pressure corresponding to that of the high pressure separator 9) by means of a pump 27, whereby substantially all of the off-gas is absorbed in the absorbate. The heat of absorption generated at this stage is removed by passing the liquid ammonia from the condenser 22 through the cooler 25, thereby preheating the liquid ammonia. By this cooling, the temperature of the high pressure absorption column is maintained at a temperature of from 120° to 180°C, preferably, of from 130° to 160°C, while the temperature of the liquid ammonia is raised to a temperature of from 100° to 160°C, preferably of from 110° to 140°C. From the top of the high pressure absorption column 24 inert gases are exhausted (which are dissolved in make-up liquid ammonia) along with only a small amount of ammonia and carbon dioxide. The exhausted gas is discharged from line 28 and may be introduced into the medium pressure absorption column 18 to recover whatever ammonia and carbon dioxide are left therein. The absorption column 24 is, for example, a heat exchanger of a vertical type, or a combination of a horizontal type heat exchanger and a packed column. With the vertical type, a packed column is not required. Moreover, the vertical type heat exchanger having an excellent absorption efficiency is very advantageous since a greater temperature differential between two heat-exchanging media is possible with the vertical type than with the horizontal type.

The pressure of the absorbate from the bottom of the high pressure absorption column 28 is raised to the urea synthesis pressure and the pressurized absorbate is introduced into the heat recovery zone 5 through line 3.

The present invention will be particularly illustrated in the following example, taken in conjunction with the sole figure, being howerver understood that the example should not be construed as limiting the invention.

EXAMPLE

Urea synthesis effluent from urea synthesis zone 6 operated at 200°C under a gauge pressure of 230 kg/cm$^2$ and containing 1,153 kg/hr of urea, 1,150 kg/hr of $NH_3$, 340 kg/hr of $CO_2$ and 550 kg/hr of $H_2O$ was passed through let-down valve 7 and line 8 and flashed into high pressure separator 9 operated under a gauge pressure of 65 kg/cm$^2$. In the separator 9, there was separated from the effluent an off-gas composed of 370 kg/hr of $NH_3$, 55 kg/hr of $CO_2$ and 22 kg/hr of $H_2O$. The depleted effluent, containing 1,150 kg/hr of urea, 782 kg/hr of $NH_3$, 285 kg/hr of $CO_2$, and 527 kg/hr of $H_2O$ was fed from the bottom of the separator 9 through reducing valve 11 and line 12 to medium pressure distillation column 13 which was operated under a gauge pressure of 17 kg/cm$^2$, thereby separating the major part of the unreacted ammonium carbamate as an off-gas containing $NH_3$ and $CO_2$ from the depleted effluent by distillation. The resulting urea solution containing the remaining ammonium carbamate was fed through reducing valve 15 and line 16 into a low pressure distillation column (not shown) wherein the remaining ammonium carbamate was separated from the urea solution by distillation. At the bottom of the low pressure distillation column, a part of the starting carbon dioxide was fed in order to accelerate the separation of the small amount of $NH_3$ remained in the urea solution at the bottom.

The thus separated urea solution was concentrated and then subjected to crystallization to obtain crystal urea product by separating it from the mother liquor.

The off-gases generated from the low pressure and medium pressure distillation stages were absorbed in the resultant mother liquor first in a low pressure absorption column (not shown) and subsequently in a medium pressure absorption column 18, to obtain an absorbate containing 114 kg/hr of urea, 370 kg/hr of $NH_3$, 330 kg/hr of $CO_2$ and 216 kg/hr of $H_2O$. At the same time, unabsorbed gaseous ammonia was obtained in an amount of 418 kg/hr.

The gaseous ammonia not absorbed in the medium pressure absorption column 18 was fed through line 21 to condenser 22 wherein it was mixed with 581 kg/hr of supplemental make-up ammonia which was introduced through line 4. The mixture was cooled to liquefaction, while the pressure of the absorbate obtained in the medium pressure absorption column 18 was raised to a gauge pressure of 65 kg/cm$^2$ and the pressurized absorbate was introduced into the high pressure absorption column 24 to absorb substantially all of the off-gas introduced from the separator 9 through the line 26, thereby obtaining a recovered ammonium carbamate solution of 130°C composed of 114 kg/hr of urea, 740 kg/hr of $NH_3$, 385 kg/hr of $CO_2$ and 238 kg/hr of $H_2O$. The heat of absorption was removed by passing through cooler 25 of the high pressure absorption column 24 recovered liquid ammonia which was liquefied in the ammonia condenser 22 and was compressed to a gauge pressure of 230 kg/cm$^2$ by means of pump 23. By the heat of absorption, the liquid ammonia was heated to 110°C. The resultant recovered ammonium carbamate solution with a pressure raised to 230 kg/cm$^2$ by means of the pump 29 was fed through line 3 to heat recovery zone 5 while the heated liquid ammonia was fed thereto through line 2. Furthermore, 717 kg/hr of $CO_2$ were compressed to a gauge pressure of 230 kg/cm$^2$ and fed through line 1 to heat recovery zone 5. The heat recovery zone 5 was provided with the cooler 5a by which steam at a gauge pressure of 4 kg/cm$^2$ was produced in an amount of 0.2 kg per kg of urea, to recover a portion of the heat of formation of ammonium carbamate thereby maintaining the temperature of the heat recovery zone at 178°C. The reaction mixture discharged from the heat recovery zone 5 was introduced into synthesis zone 6 to convert ammonium carbamate into urea.

What is claimed is:

1. In a process for recovering unreacted ammonium carbamate contained in the effluent obtained by reacting at urea synthesis temperatures and pressures carbon dioxide with ammonia in stoichiometric excess, wherein said effluent is subjected to a first ammonium carbamate decomposition stage at a gauge pressure of from 40 to 120 kg/cm$^2$, then to a second ammonium carbamate decomposition stage at a gauge pressure of from 10 to 25 kg/cm$^2$ and finally to a third ammonium carbamate decomposition stage at a gauge pressure of below 5 kg/cm$^2$, thereby forming an off-gas in each stage and wherein the off-gases from at least said first and second stages are absorbed in an absorbent selected from the group consisting of water, aqueous ammonia, aqueous urea, aqueous ammonium carbamate and an aqueous solution containing urea and ammonium carbamate, the resultant recovered ammonium carbamate solution being recirculated to the urea synthesis, the improvement which comprises absorbing said off-gas from said second decomposition stage in said absorbent to form an ammonium carbamate containing absorbate and unabsorbed gaseous ammonia; cooling said unabsorbed gaseous ammonia, to form recovered liquid ammonia; absorbing in said ammonium carbamate containing absorbate pressurized to the pressure substantially equal to that of said first decomposition stage substantially all of said off-gas from said decomposition stage at a temperature of from 120° to 180°C while removing the heat of absorption by indirect heat exchange with a mixture of make-up liquid ammonia and said recovered liquid ammonia pressurized to said urea synthesis pressure, whereby said recovered ammonium carbamate solution is formed and said mixture of said make-up liquid ammonia and said recovered liquid ammonia are heated to a temperature of from 100° to 160°C; reacting said mixture of said make-up liquid ammonia and said recovered liquid ammonia and said recovered ammonium carbamate solution with make-up carbon dioxide in a heat recovery zone to form a reaction mixture containing ammonium carbamate while concurrently removing from said zone the surplus heat of reaction by indirect heat exchange; and introducing said formed reaction mixture containing ammonium carbamate to the urea synthesis.

2. A process as claimed in claim 1, wherein said unabsorbed gaseous ammonia is mixed with make-up liquid ammonia and then cooled to liquefy said gaseous ammonia.

3. A process as claimed in claim 1, wherein said first decomposition stage is conducted without externally heating said urea synthesis effluent.

4. A process as claimed in claim 1, wherein unabsorbed inert gas contained in said off-gas from the first decomposition stage and containing a slight amount of ammonia and carbon dioxide is contacted with said absorbent together with said off-gas from said second decomposition stage to recover said ammonia and carbon dioxide.

5. A process as claimed in claim 1, wherein the off-gas from said third decomposition stage is absorbed in said absorbent and the resultant absorbate absorbs said off-gas from said second decomposition stage.

* * * * *